US007717870B2

(12) United States Patent
Becerra et al.

(10) Patent No.: US 7,717,870 B2
(45) **Date of Patent: *May 18, 2010**

(54) SYSTEM AND METHOD FOR PROVIDING DECOMPRESSION MODALITIES USING OSCILLATORY SIGNALING AT HIGH TENSION LEVELS AND SMOOTH TRANSITION SIGNALING FOR SPINAL TREATMENT

(75) Inventors: Carlos Becerra, Atlanta, GA (US); Markus Randel, Ball Ground, GA (US)

(73) Assignee: North American Medical Corporation, Marietta, GA (US)

( * ) Notice: Subject to any disclaimer, the term of this patent is extended or adjusted under 35 U.S.C. 154(b) by 1479 days.

This patent is subject to a terminal disclaimer.

(21) Appl. No.: 11/025,802

(22) Filed: Dec. 29, 2004
(Under 37 CFR 1.47)

(65) Prior Publication Data

US 2005/0192517 A1 Sep. 1, 2005

Related U.S. Application Data

(60) Provisional application No. 60/533,182, filed on Dec. 30, 2003, provisional application No. 60/604,989, filed on Aug. 27, 2004.

(51) Int. Cl.
*A61F 5/00* (2006.01)

(52) U.S. Cl. .......................................... 602/32; 602/36

(58) Field of Classification Search ............. 602/32–40; 5/624, 648, 650
See application file for complete search history.

(56) References Cited

U.S. PATENT DOCUMENTS

| | | | | |
|---|---|---|---|---|
| 3,898,985 | A * | 8/1975 | Butcher et al. | 601/146 |
| 6,986,181 | B2 * | 1/2006 | Murphy et al. | 5/648 |
| 7,189,214 | B1 * | 3/2007 | Saunders | 602/32 |
| 2002/0128576 | A1 * | 9/2002 | Mayes | 602/33 |

* cited by examiner

*Primary Examiner*—Michael A. Brown
(74) *Attorney, Agent, or Firm*—Bryan W. Bockhop; Bockhop & Associates, LLC

(57) ABSTRACT

A modality system that computes a signal having a first tension level, a second tension level, and transition tension levels between the first and second tension level, where the higher of the first and second tension levels includes an oscillation. The system communicates the signal to an electromechanical actuator to apply a modality treatment to a patient.

11 Claims, 14 Drawing Sheets

FROM FIG. 4A

SYSTEM AND METHOD FOR PROVIDING DECOMPRESSION MODALITIES USING OSCILLATORY SIGNALING AT HIGH TENSION LEVELS AND SMOOTH TRANSITION SIGNALING FOR SPINAL TREATMENT

CROSS-REFERENCES TO RELATED APPLICATIONS

This application claims priority from U.S. Provisional Patent Application Ser. Nos. 60/533,182 filed Dec. 30, 2003 and 60/604,989 filed Aug. 27, 2004, the entire teachings of which are herein incorporated by reference.

BACKGROUND OF THE INVENTION

Treatment of back pain by therapists is typically performed manually and/or by use of modality machines or systems. Such treatment is generally known as a modality, which includes the physical treatment of a disorder. Back pain may be the result of a number of different reasons, including degenerative disc disease, herniated disc, posterior facet syndrome, sciatica, specific injury, etc. In the case of treating back pain, a number of modality treatments may be performed, including spinal traction and spinal decompression. There are generally two types of spinal decompression, including intradiscal or intervertebral disc decompression (IDD) and muscular or ligament decompression (conventional). Traction and decompression modality treatments are generally understood to be types of spinal distraction techniques. Traction and decompression are considered general terms that do not necessarily include intradiscal disc decompression. Traction generally is performed by pulling to a maximum or predetermined high tension level for a period of time (e.g., 30 minutes) and then releasing. Conventional decompression involves cycling between a high or predetermined level of tension (e.g., 24 pounds) and a lower level of tension (e.g., 18 pounds). The cycling between the high and lower tension levels is generally performed over a predetermined duration of time (e.g., 30 minutes) with multiple durations of high and low tension level intervals (e.g., six minute intervals).

Modality treatment is generally based on specific back pain that a patient is suffering. For example, disc injuries of the spinal column may be treated using conventional decompression to facilitate natural reparation of the disc. The use of conventional decompression provides for release or relaxation of paraspinal muscles, which are involuntary muscles that operate to maintain 4000 Newtons of pressure between each vertebrae by confusing the paraspinal muscles via the high and low tension level cycling. By relaxing these paraspinal muscles, the vertebrae are able to be manipulated or separated so that needed healing fluids are able to reach the disc (in the case of a dehydrated or injured disc) or the disc is able to be realigned (in the case of a slipped disc), for example.

While conventional decompression treatment profiles have been incorporated into the modality machines, the modality machines are still problematic for many patients with severe injuries or sensitivity problems because the conventional decompression, in general, does not perform intradiscal disc decompression. In these and other cases, patients are incapable of being treated with modality machines due to certain pain issues, such as pinched nerves or paraspinal muscles that do not satisfactorily release by using conventional decompression techniques. Often, even the slightest surge in acceleration may cause significant discomfort for the patients with pain sensitivity problems. In these cases, manual manipulation is generally used to treat the patients. What is needed is a modality machine that uses intradiscal disc decompression techniques that more closely resembles manual manipulation to allow the patient with higher sensitivity (e.g., more pain issues) to be treated with a machine. In addition, there is a need for the modality machine to internally activate dry or partially dry discs with intradiscal substances for reparation of the discs during treatment.

SUMMARY

To overcome the problems of modality machines using conventional decompression techniques for treating patients with spinal injuries, a modified decompression technique that includes using a smooth transition between tension levels may be utilized to provide more effective treatments, especially to patients who have acute pain or pain sensitivity problems. The modified decompression technique operates to perform an intradiscal disc decompression where the paraspinal muscles first relax and then the intervertebral disc decompression may occur. The smooth transition may be performed by utilizing a sinusoidal mathematical function, such as a cosine, so that the use of a convention electromechanical actuator provides a smooth transition (see FIG. 6) as compared to using a ramp function (see FIGS. 2 and 5) extending between high and low tension levels. The use of a smooth transition substantially eliminates a step or other discontinuity function in an electromechanical system due to the responsiveness of the electromechanical system used in modem modality machines. In addition, an oscillation at high tension may be used to further relax the paraspinal muscles. The modality machine that includes either or both smooth transition and oscillation at high tension levels more closely resembles internal manual modality treatment and allows for additional and faster relaxation of paraspinal muscles, thereby enabling patients with higher pain sensitivity to be treated with the modality machine operating the modified decompression technique.

In one embodiment, the principles of the present invention includes a modality system that computes a signal having a first tension level, a second tension level, and transition tension levels between the first and second tension level, where the higher of the first and second tension levels includes an oscillation. The system communicates the signal to an electromechanical actuator to apply a modality treatment to a patient.

In another embodiment, the principles of the present invention includes a modality system and method for performing modality treatments on patients. The modality system may compute a signal having a first tension level, a second tension level, and transition tension levels between the first and second tension levels. At least a portion of the transition tension levels may form a curve. The signal may be communicated to an electromechanical actuator to apply a modality treatment to a patient.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION OF THE DRAWINGS

Figure 1:
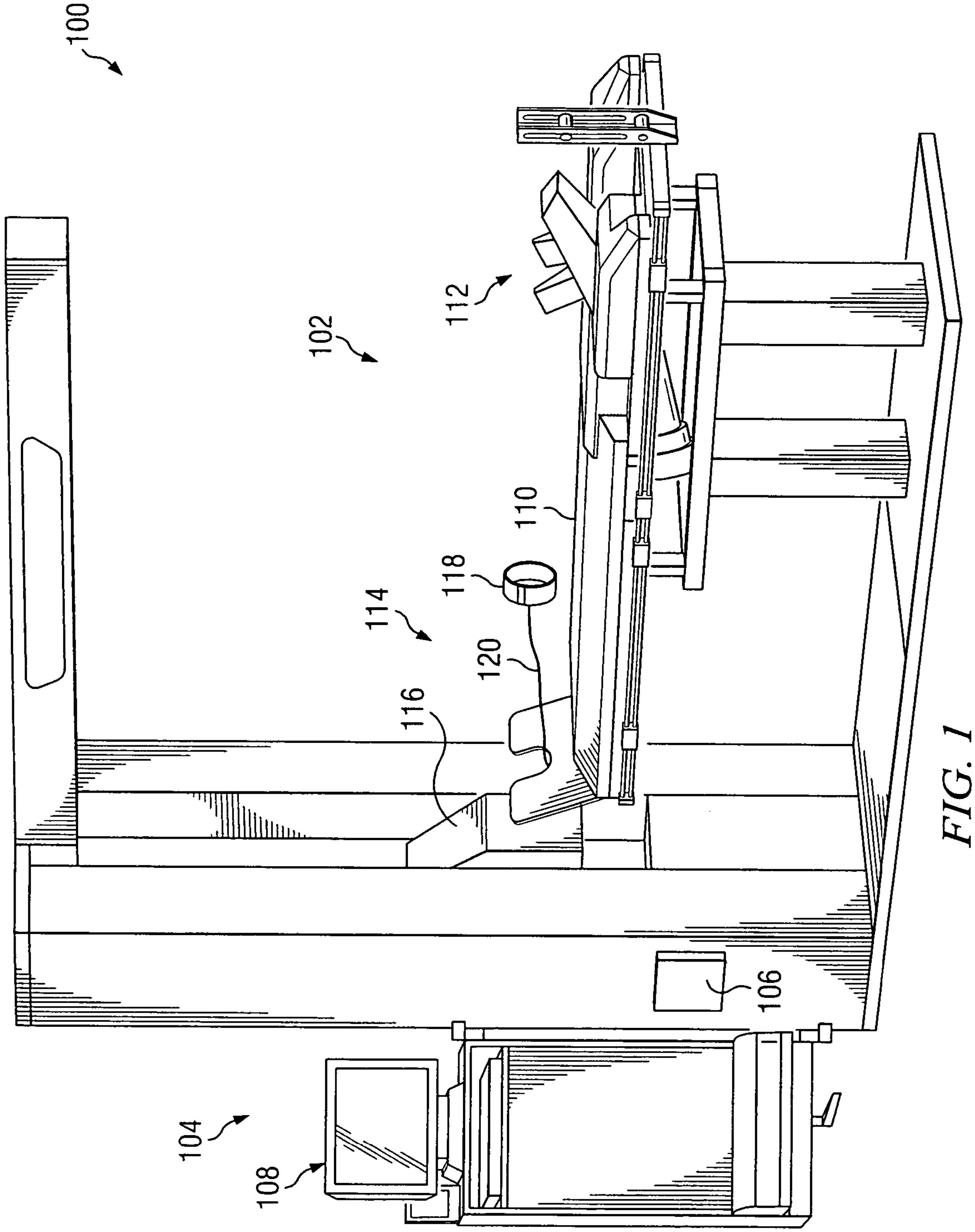
FIG. 1 is an illustration of an exemplary modality machine for performing modality treatments utilizing the principles of the present invention.

FIG. 1 is an illustration of an exemplary modality machine 100 for performing modality treatments utilizing the principles of the present invention. The modality machine 100 includes a mechanical portion 102 and an electronic portion 104 that includes a computing unit or controller 106 and operator interface 108. The computing unit 106 is electrically coupled to the mechanical portion 102 of the modality machine 100 and executes software (described in FIGS. 3-4 and 7-8) for performing modality treatments on patients.

The mechanical portion 102 may include a table or bed assembly 110 having a head end 112 and a foot end 114. A decompression head 116 may be fixedly positioned with respect to the table 110 (e.g., located at the foot end 114) and include one or more electromechanical actuator (not shown) for applying and/or adjusting tension to a patient engaging member 118 via a coupling member 120. The electromechanical actuator(s) may include a motor, DC or AC, linear actuator, hydraulic actuator, pneumatic actuator, or any other, electromechanical actuator capable of applying tension up to 100 pounds or more for performing modality treatments as understood in the art. It should be understood that other hardware, such as gears, may be included in the decompression head 116 for enabling operation of the electromechanical actuator. In one embodiment, the electromechanical actuator in the decompression head is a medical class motor as understood in the art. The medical class motor may drive gears having a gear ratio of 300 or higher to provide high precision. The coupling member 120 may be a cable or other device utilized to apply tension from the decompression head 116 to a device that engages the patient, such as the patient engaging member 118.

The computing unit 106 may be in communication with the decompression head 116 to communicate a signal or modality profile defined by an operator, such as a physical therapist, utilizing the operator interface 108. In general, a modality profile is a signal that is used to command an electromechanical actuator to apply tension levels to a coupling member 118 during a modality treatment. Specific examples of modality profiles are further shown in FIGS. 2 and 6 in accordance with the principles of the present invention.

In performing a modality treatment, a patient may lie on the table 110 with his or her head at the head end 112 and have the patient engaging member 118 secured to the patient for the particular modality treatment to be applied as understood in the art. An operator of the modality machine defines or selects a modality profile for the modality treatment to be applied to the patient via the operator interface 108. The computing unit 106 may compute a modality profile real-time (i.e., during the modality treatment) or predetermine the modality profile. In controlling the decompression head 116, the computing unit 106 may communicate signals representing the modality profile to the decompression head 116 to increase, decrease, and/or maintain tension on an anatomical structure of the patient. For example, when applying a modality treatment to the lumbar region of the patient's spinal column, the patient lies with his or her head on the head end 112 and a chest harness (not shown) is applied across the chest of the patient for securing the patient to the bed assembly 110. The patient engaging member 118, which in this case is a pelvic harness, is applied to the pelvic region of the patient and attached to the electromechanical actuator in the decompression head 116. The computing unit communicates the signal to the decompression head 116 to produce tension in response to signals to adjust tension to the pelvic harness to apply tension for decompressing the lumbar region of the patient.

In generating the signals, software is executed on the computing unit 106. It should be understood that the operator interface 108 may communicate with a computing unit (not shown) that executes the software for controlling the decompression head 116. The software may also be utilized to manage the modality machine 100 and perform other processes. The computing may be performed on an external computing unit or on an embedded one, such as the computing unit 106. Alternatively, distributed computing units located on the modality machine 100 could be utilized to execute the software. Feedback sensors (not shown) located on the decompression head 116 or other structure located on or coupled to the bed assembly 110 may be used to sense tension and/or other modality parameters for feeding back to the computing unit 106 for more precise control of the decompression head 116.

Figure 2:
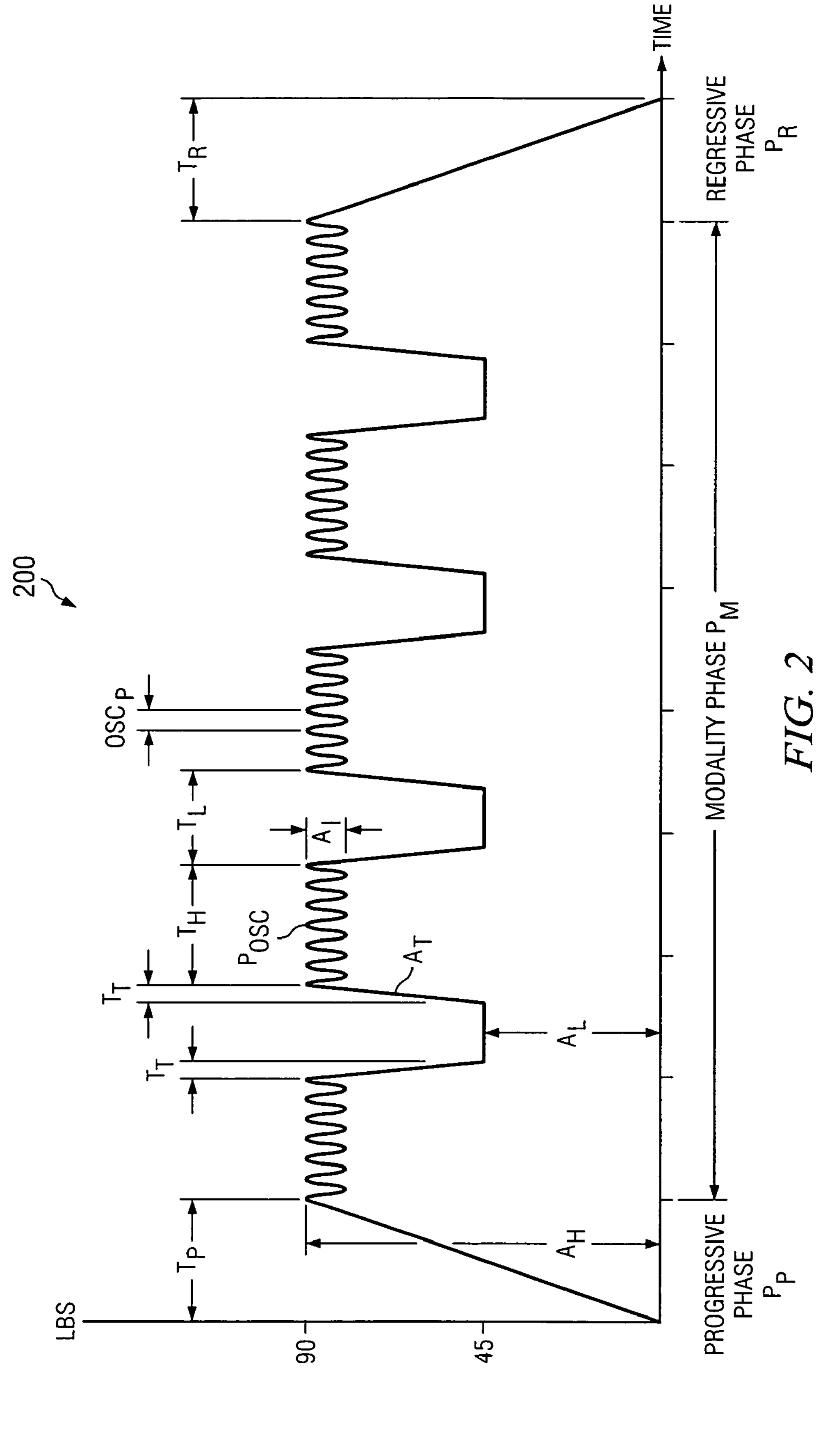
FIG. 2 is an illustration of an exemplary waveform that represents a modality profile that is computed by a computing unit for driving a decompression head of the modality machine of FIG. 1.

FIG. 2 depicts an exemplary waveform or signal that represents a modality profile 200 that is computed by a computing unit of the modality machine 100 for driving the decompression head 116 (FIG. 1). The modality profile 200 describes force or tension to be applied to the decompression head 116 for performing a modality treatment to a patient being treated on the modality machine 100. The waveform is described by a number of parameters that define different phases of the modality treatment, including (i) progressing phase or ramp-up $P_P$, (ii) regressive phase or ramp-down $P_R$, and (iii) modality phase $P_M$. The progressive phase $P_P$ identifies a progressive time $T_P$ or portion of the modality treatment that the modality machine 100 starts the modality treatment on the patient. The regressive phase $P_R$ identifies a regressive time $T_R$ or portion of the modality treatment that the modality machine 100 ends the modality treatment on the patient. The modality phase $P_M$ identifies high times $T_H$, low times $T_L$, and transition times $T_T$ or portions of the modality treatment that the modality machine 100 performs a modality treatment on the patient.

During the modality phase $P_M$, the modality profile 200 includes a number of different tension levels, including a high tension level $A_H$, low tension level $A_L$, transition tension levels $A_T$ between the high and low transition levels $A_H$ and $A_L$, and oscillation tension levels $A_{OSC}$ defined by the high tension level $A_H$ offset by an oscillation. The offset may mathematically add, subtract, or otherwise and have a selectable oscillation intensity level $A_I$. In one embodiment, the high tension level $A_H$ may be set to 90 pounds, low tension level $A_L$ may be set to 45 pounds, and oscillation intension level $A_I$ set to 10 pounds. In addition, an oscillation period $OSC_P$ may be defined for the modality treatment. In one embodiment, the oscillation period $OSC_P$ may be set at 0.1 seconds, having a frequency period of 10 cycles per second (i.e., 10 Hz). As understood in the art, the high and low tension levels $A_H$, $A_L$, oscillation intensity level $A_I$, and oscillation period $OSC_P$ may be set to any level that a physician and/or therapist believes is best to treat the patient for back pain. In one embodiment, the oscillation intensity level $A_I$ may range from 5 to 20 pounds. By oscillating the high tension level $A_H$, a dithering effect is created that causes the paraspinal muscles of patients with the highest pain sensitivity to learn to accept the modality treatment more readily as the oscillation causes the paraspinal muscles to be confused and relax. Thereafter, intradiscal or intervertebral disc decompression treatment may occur. It should be understood that an oscillation may additionally be applied to the transition and low tension levels.

The transitions between different levels are shown as ramps. The slopes may vary in steepness based on a ramp time that may be set by an operator. Alternatively, the transition between tension levels may be stepped. It should be understood that the modality profile 200 is merely exemplary and that numerous other modality profiles that include an oscillation at the high tension level $A_H$ may be utilized according to the principles of the present invention. In another embodiment, the oscillation intensity level $A_I$ may vary during each high time $T_H$ (e.g., increase between five and ten pounds).

Figure 3A:
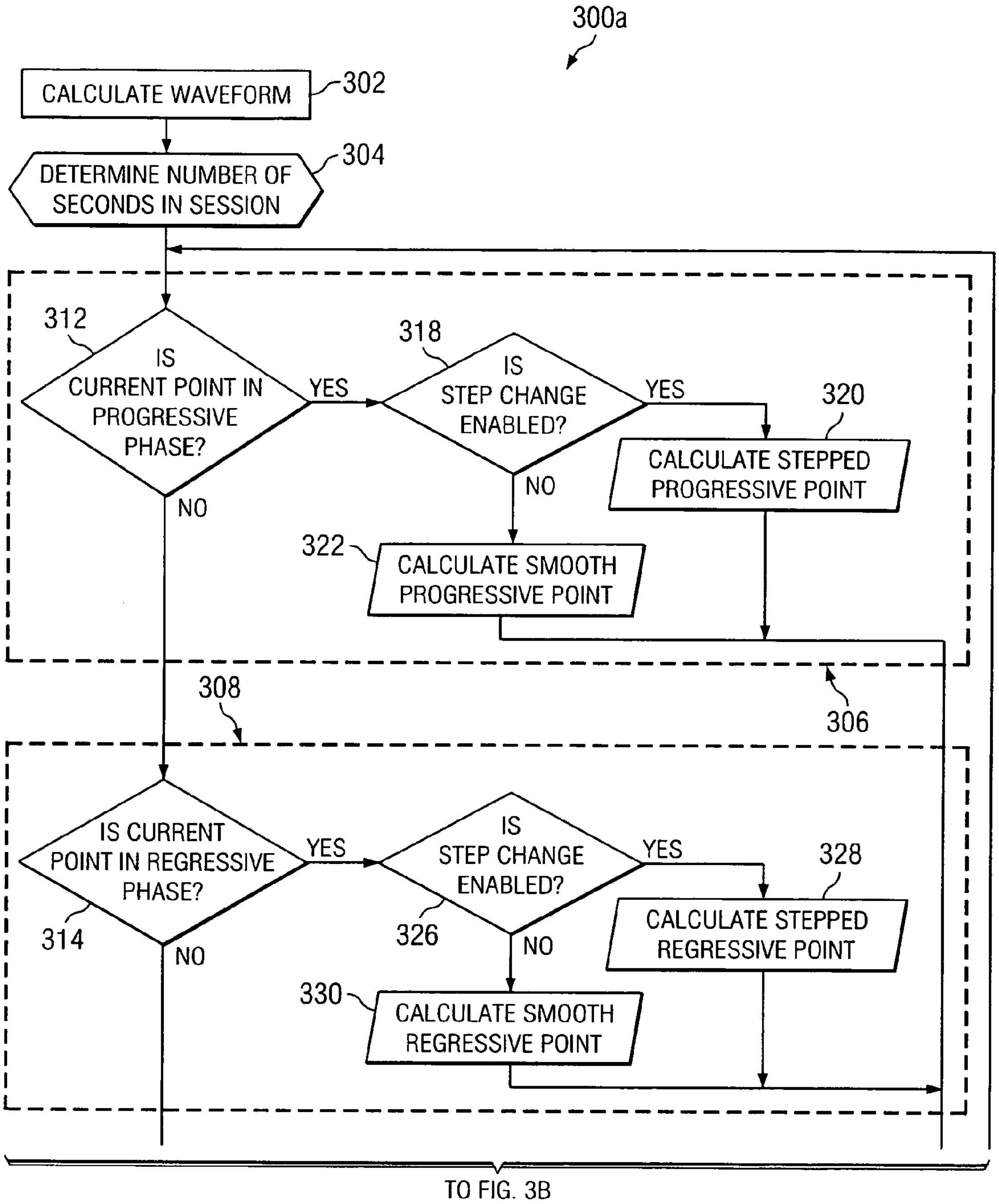
FIGS. 3A-3B (collectively FIG. 3) are flow diagrams of an exemplary algorithm that may be encoded into software to be executed by a modality machine to generate a modality profile, such as the modality profile of FIG. 2, that applies an oscillation to the high tension level during a modality treatment.
Figure 3B:
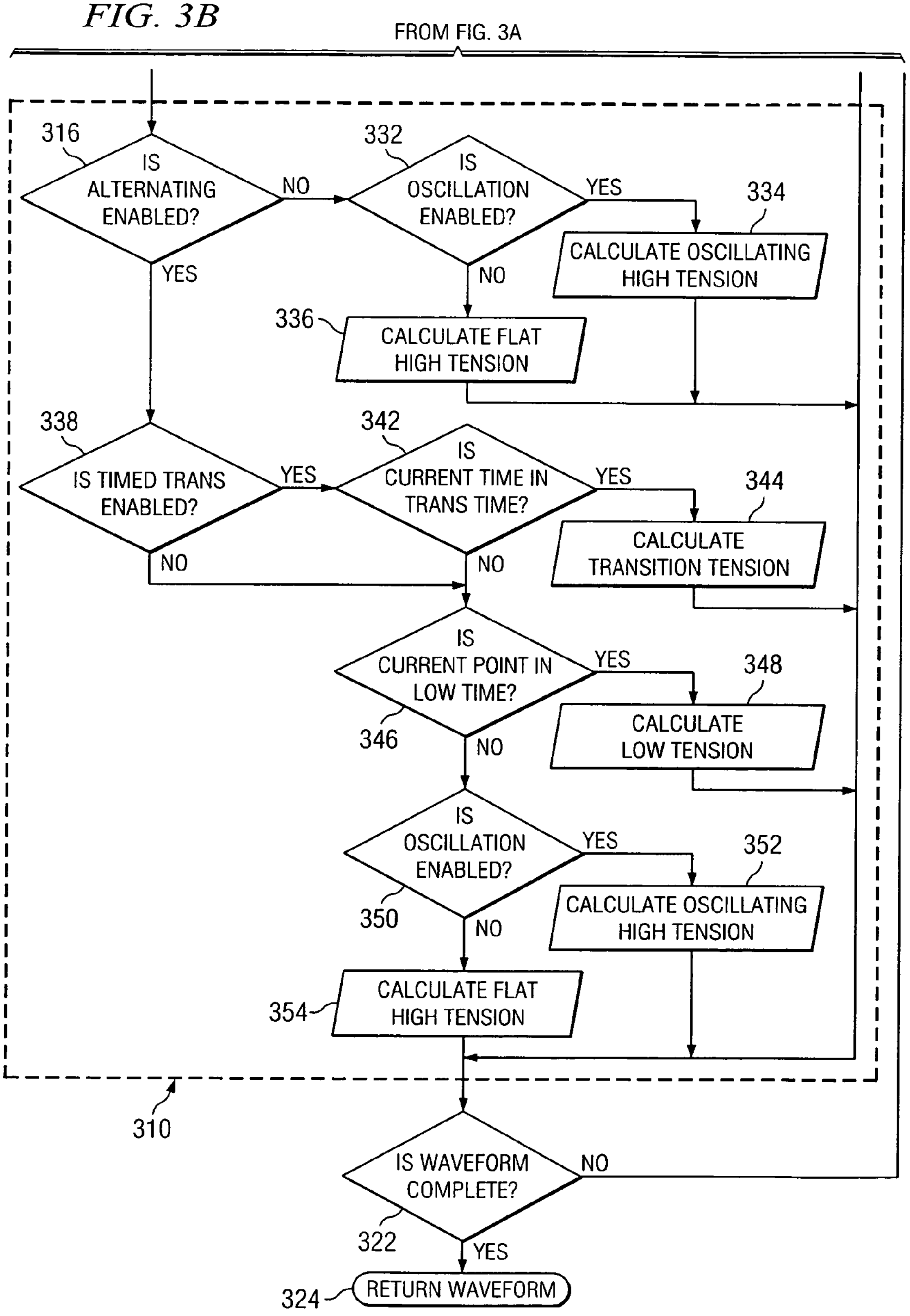

FIG. 3 is a flow diagram of an exemplary algorithm 300*a* that may be encoded into software to be executed by a modality machine to generate a modality profile, such as the modality profile 200 of FIG. 2, that applies an oscillation to the high tension level during a modality treatment. The algorithm 300*a* describes a process that computes a signal or waveform composed of data points representative of tension levels or other parameters that may be utilized to control electromechanical actuator(s) at each point in time during a modality treatment. The algorithm 300*a* starts at step 302. At step 304, the number of seconds in the modality treatment or session is determined. The determination may be based on an input from an operator or based on a treatment program previously entered. Modality treatments may be input in minutes and the number of seconds is calculated by multiplying by 60 seconds/minute. The signal for the modality treatment used for driving an electromagnetic actuator may be computed for each second or fraction of a second. For example, the modality treatment may be thirty (30) minutes, so every second or fraction of a second may be defined as a time differential to compute a data point or signal level that is, in turn, used to drive an electromechanical actuator.

The algorithm 300*a* computes a signal representative of the modality profile for performing a modality treatment substantially real-time or prior to performing the modality treatment on a patient. In computing the signal substantially real-time, one calculation per data point is performed at each time interval during treatment, thereby minimizing the amount of data storage for the waveform. If the waveform is computed prior to performing the modality treatment on the patient, then the algorithm may preprocess the waveform for storage, but additional memory is utilized to store each data point of the waveform.

Continuing on with FIG. 3, there may be three basic phases to a modality treatment (see, FIG. 2), the progressive phase $P_P$, regressive phase $P_R$, and modality phase $P_M$. The algorithm 300*a* defines the process by which a signal may be computed for each of the different phases (e.g., progressive $P_P$, regressive $P_R$, modality $P_M$), identified by algorithm sections 306, 308, and 310. The algorithm 300*a* operates based on time for computing the data points for the signal. Accordingly, as a time counter increases, the algorithm 300*a* determines whether to make a computation for a tension level in the progressive phase $P_P$ at step 312, regressive phase $P_R$ at step 314, or default to the modality phase $P_M$ at step 316.

If it is determined that the current time is within the progressive phase $P_P$ at step 312, then a determination may be made as to whether a step change is enabled at step 318. A step change enables the signal to be calculated in the progressive phase between zero and a high tension level $A_H$ (see, FIG. 2) due to the patient having less pain sensitivity. If the step change is enabled, a stepped progressive point of the signal is calculated at step 320. If the step change is not enabled, a smooth progressive point is calculated at step 322. The smooth progressive point that is calculated is more mathematically intensive and may or may not be calculated using a linear function. For example, if the calculation is linear, then the ramp may be a more gradual ramp that takes longer to reach the high tension level $A_H$. In either case, the process continues at step 322, where a determination is made as to whether the waveform and/or modality session is complete. If the waveform is complete (i.e., the modality treatment session time is complete), then the algorithm 300*a* ends at step 324. Alternatively, the process repeats back to step 312.

If it is determined that the current time is within the regressive phase $P_R$ at step 314, then a determination may be made as to whether a step change is enabled at step 326. If the step change is enabled, a stepped regressive point of the signal is calculated at step 328. If the step change is not enabled, a smooth regressive point is calculated at step 330. Similar to the progressive phase calculations, the smooth regressive point calculation may be performed utilizing a non-linear or linear calculation to substantially eliminate abrupt tension increases or decreases, thereby making the modality treatment more comfortable for patients who have sensitivity or acute pain problems.

If the current time is neither in the progressive phase $P_P$ or regressive phase $P_R$, then the algorithm defaults to compute the data points of the signal for the modality phase $P_M$ at step 316. The modality phase $P_M$ has several control options that may be set by an operator for a modality treatment, including setting (i) sequential tension level alternation, (ii) time transitions, and (iii) oscillation at the high tension level $A_H$. If at step 316, it is determined that the control option for alternating tension levels is not enabled (i.e., traction modality selected) at step 316, then a determination is made as to whether the control option for oscillating at high tension is enabled at step 332. If so, then a calculation for oscillation at high tension level is performed at step 334. In one embodiment, the oscillation is computed using a sinusoidal function. Alternatively, the oscillation may be computed utilizing a non-sinusoidal function, such as a triangle or other non-sinusoidal, mathematical function. Alternatively, a conventional, flat, high tension level $A_H$ is calculated at step 336. In either case, the process continues at step 322 to determine whether the waveform is complete.

If the control option of alternating the tension levels is selected (i.e., decompression modality selected at step 316), then a determination is made at step 338 as to whether the control option for timed transition is enabled. If so, then at step 340, a determination is made as to whether the current time is in a transition time $T_T$ at step 342. If the current time is in the transition time $T_T$, then a transition tension level is calculated at step 344. The transition tension level may be any tension level between the low and high tension levels $A_L$ and $A_H$. Otherwise, the process continues at step 346 where a determination is made as to whether the current time is in a low time $T_L$. If so, then a low tension level $A_L$ is calculated at step 348. Otherwise, a determination is made at step 350 as to whether a control parameter for oscillation is enabled. If the oscillation control parameter is enabled, then an oscillating high tension level is calculated at step 352. The oscillation may be calculated using a sinusoidal function or non-sinusoidal function as understood in the art. If it is determined at step 350 that the oscillation control parameter is not enabled, then a flat or constant high tension level $A_H$ is calculated at step 354. After calculating the low or high tension level, the process continues at step 322.

Figure 4A:
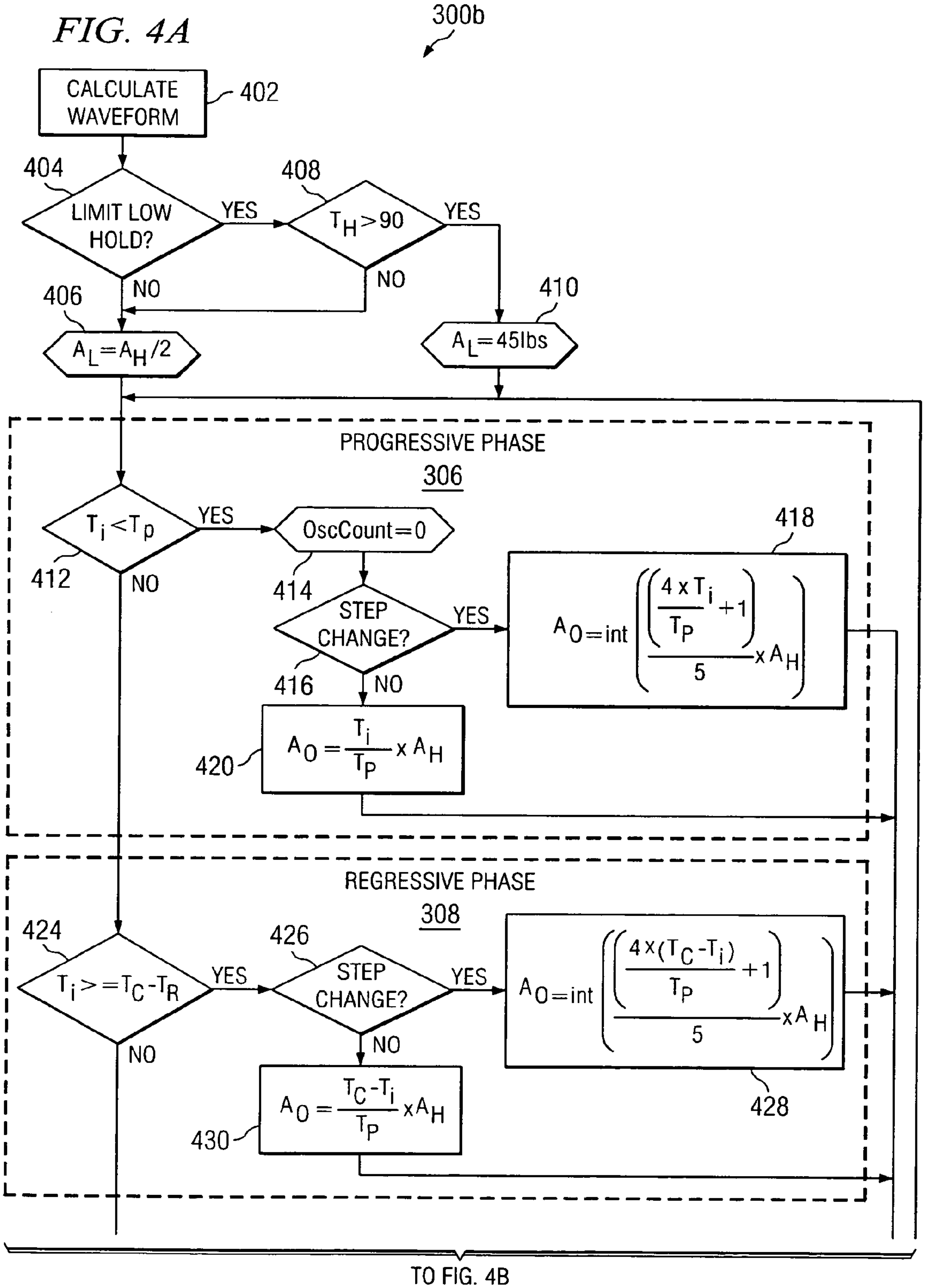
FIGS. 4A-4C (collectively FIG. 4) are more detailed flow diagrams that describe an exemplary algorithm including exemplary formulas for generating a signal or waveform including oscillations on the high tension level for a modality treatment.
Figure 4B:
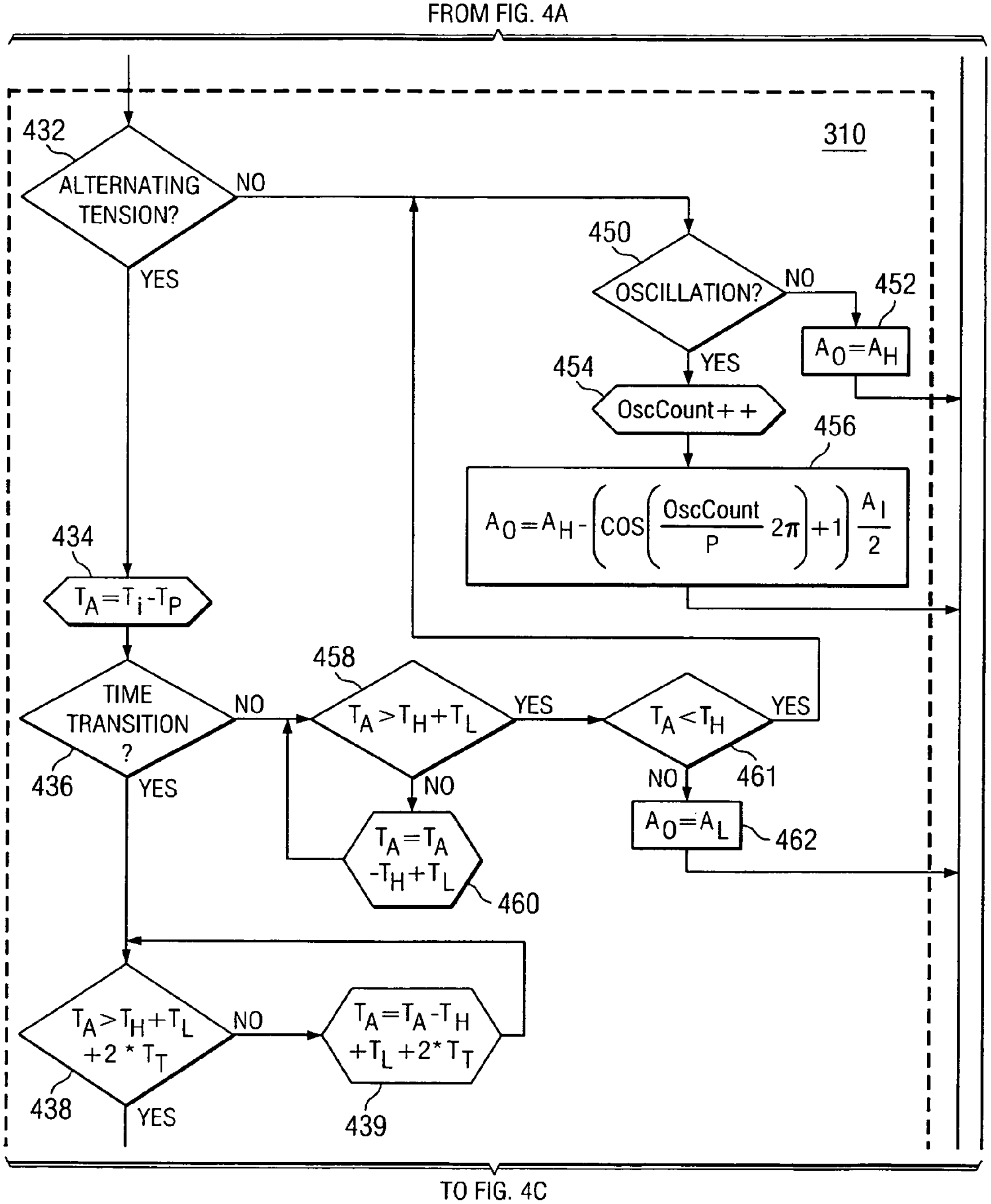
Figure 4C:
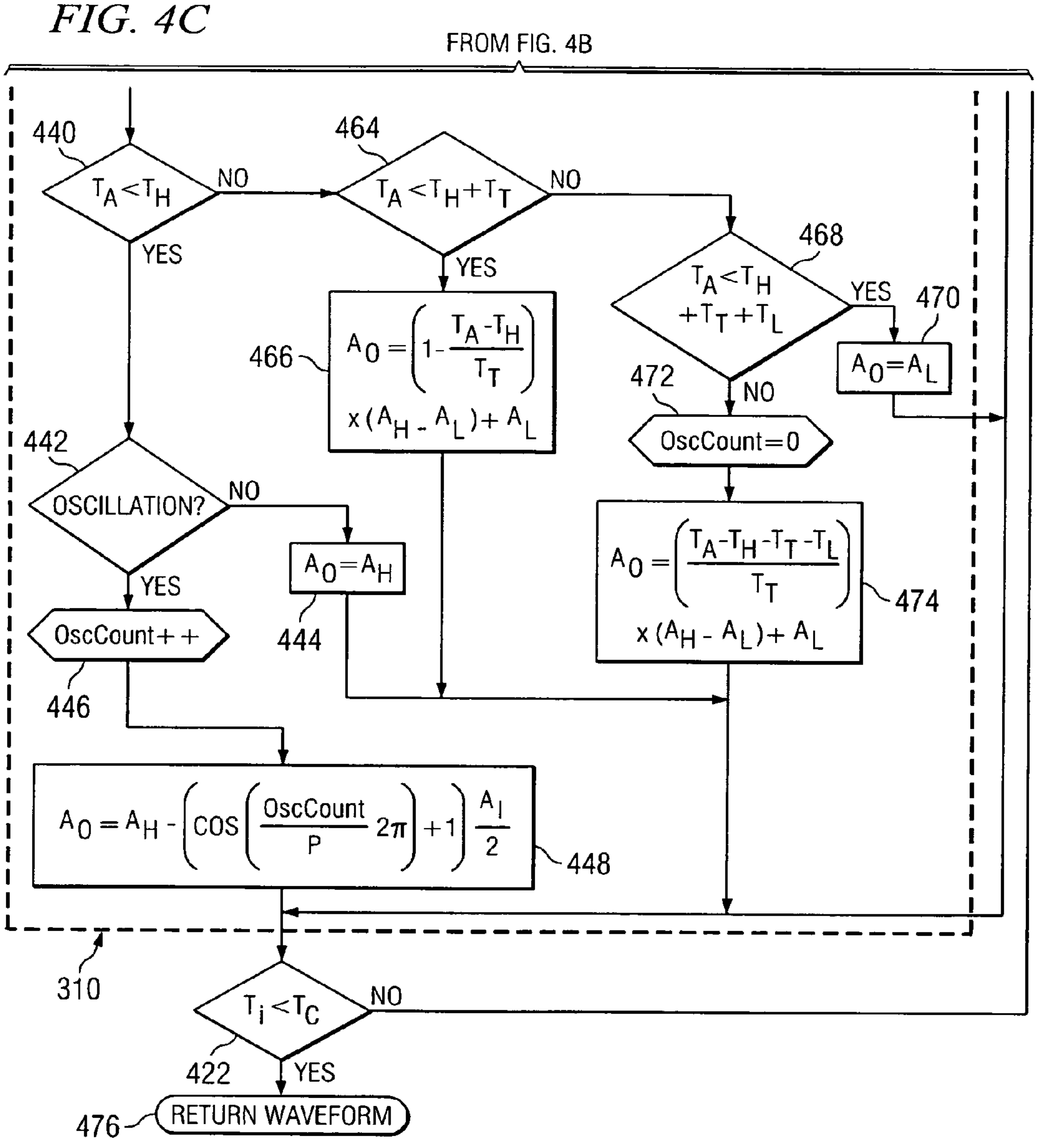

FIG. 4 is a flow diagram of an exemplary algorithm 300*b* that includes mathematical details of the algorithm 300*a* of FIG. 3 for generating a waveform including oscillations on the high tension levels for the modality treatment. The algorithm sections 306, 308, and 310 correlate with the algorithm 300*a* of FIG. 3, where algorithm section 306 represents an embodiment for generating a waveform for the progressive phase $P_P$ (FIG. 2), algorithm section 308 represents an embodiment for generating a waveform for the regressive phase $P_R$, and algorithm section 310 represents an embodiment for generating a waveform for the modality phase $P_M$ that may include generating an oscillation at a high tension level $A_H$.

Prior to starting the modality treatment, a number of control parameters may be set by an operator of the modality machine utilizing a graphical user interface (GUI) or otherwise (e.g., physical knobs and switches). The control parameters are shown in TABLE I, which includes a description of the functionality of the different control parameters. The algorithm 300*b* employs certain functions, such as oscillation at the high tension level, based on the settings of the control parameters in generating a modality profile to provide a modality treatment to a patient. TABLE II identifies system and output variables for controlling electromechanical actuator(s) of the modality system.

TABLE I

Control Parameters

| CONTROL PARAMETER | FUNCTION |
|---|---|
| STEP ENABLED | Step modality profile from one tension level to another |
| OSCILLATION ENABLED | Oscillate modality profile at a high tension level |
| ALTERNATING ENABLED | Alternate modality profile between high and low tension levels |
| TIME TRANSITION ENABLED | Transition flag |

TABLE II

System and Output Parameters Used In Modality Algorithm

| Variable | Name | Units |
|---|---|---|
| $A_O$ | Output Tension | Unit Pounds (lbs) |
| $A_H$ | High Tension | Unit Pounds (lbs) |
| $A_L$ | Low Tension | Unit Pounds (lbs) |
| $A_I$ | Oscillation Intensity | Unit Pounds (lbs) |
| $T_i$ | Current Time | Seconds |
| $T_C$ | Session Time | Seconds |
| $T_P$ | Progressive Time | Seconds |
| $T_R$ | Regressive Time | Seconds |
| $T_H$ | High Time | Seconds |
| $T_L$ | Low Time | Seconds |
| $T_T$ | Transition Time | Seconds |
| P | Oscillation Period | Cycles/Min |

The waveform generation process starts at step 402. At step 404, a determination is made as to whether a limit low hold is to occur, meaning to set the low tension level $A_F$ to a lower resting level if the high tension level $A_H$ is maintained for more than a certain duration. If not, then the low tension level $A_L$ is set to half of the high tension level ($A_H/2$) at step 406. Otherwise, if the high time $T_H$ is greater than 90 (seconds) as determined at step 408, then the low tension level $A_L$ is set to 45 pounds at step 410. If the high time $T_H$ is less than 90, then the low tension level is set to half of the high tension level ($A_H/2$). Although not shown, the number of seconds of the modality treatment session $T_C$ may be determined in this portion of the algorithm 300*b* as indicated in the more general algorithm 300*a* or prior to entering the algorithm 300*b*. In one embodiment, determining the number of seconds in the modality treatment session is performed by accessing a memory location that stores the value set by an operator.

The process of the algorithm 300*b* continues at step 412 in the algorithm section 306 for computing values for the waveform in the progressive phase $P_P$. At step 412, a counter maintaining current time $T_i$ is compared with a variable storing progressive time $T_P$. If the current time $T_i$ is less than the progressive time $T_P$, then the modality system performs an initialization by setting oscillation counter OscCount to zero at step 414. If it is determined that a step control parameter is set at step 416, then a data point of the modality profile signal may be computed by the equation at step 418 for stepping the tension level to a high tension level $A_H$. Otherwise, the equation at step 420 may be computed to ramp the tension level during the progressive phase $P_P$ to the high tension level $A_H$.

The algorithm continues at step 422 to determine if the current time $T_i$ is less than the modality treatment session time $T_C$. If not, then the process loops to step 412 until the current time $T_i$ is equal to the modality treatment session time $T_C$. It should be understood that other conditions may additionally and/or alternatively be utilized to end the modality treatment, including an emergency shutoff determined by the modality system via hardware or software, emergency shutoff initiated by the patient, and shutoff initiated by the operator.

If it is not determined that the current time is in the progressive phase $P_P$ at step 412, the process continues at step 424 to determine if the current time $T_i$ is in the regressive phase $P_R$. If so, then at step 426, the step change control parameter is checked to determine if the tension level is to be stepped. If so, then the equation at step 428 may be utilized to compute the tension level $A_O$ at the current time $T_i$ during the regressive phase $P_R$. Alternatively, the equation at step 430 may be utilized to ramp down the tension from the high tension level $A_H$ to a tension level of zero. The process continues at step 422 until the current time $T_i$ equals the modality treatment session time $T_C$.

If the current time $T_i$ is neither in the progressive or regressive phase, then it is assumed to be in the modality phase $P_M$. A determination is made at step 432 as to whether a control parameter for alternating tension is set at step 432. If so, then the process continues at step 434 where an alternating time variable $T_A$ is set based on the current time $T_i$ and progressive time $T_P$. If it is determined at step 436 that a timed transition control parameter is set, then the process continues at step 438, where a determination is made as to whether the current time is in a transition time based on the alternating time variable $T_A$. If not, then the alternating time variable $T_A$ is repeatedly adjusted at step 439 for normalization purposes. Once in a transition time $T_T$, then the process continues at step 440 to determine if the alternating time variable $T_A$ is less than the high time $T_H$. If so, then at step 442, a determination is made as to whether a control parameter for performing oscillation at the high tension level $A_H$ is set. If not, then at step 444, the output tension level $A_O$ is set to a constant high tension level $A_H$. Otherwise, the oscillation counter OscCount is increased at step 446 and an oscillation value is computed for the waveform at the current time $T_i$ at step 448. In one embodiment, the oscillation is computed utilizing a sinusoidal function, and more particularly, a cosine function. It should be understood that other oscillatory functions may be utilized, including a triangle function, sine function, sawtooth function, etc. The process continues at step 422 to determine if the current time $T_i$ is equal to the modality treatment session time $T_C$.

If at step 432 it is determined that the control parameter for alternating tension is disabled so that the modality treatment is to have a traction profile, then the process continues at step 450. At step 450, a determination is made as to whether the control parameter to perform oscillation at the high tension level $A_H$ is set. If not, then the output tension level $A_O$ is set to a constant $A_H$ at step 452. Otherwise, the counter OscCount is increased at step 454 and a computation is made to subtract an oscillatory function from the high tension level $A_H$ at step 456. In one embodiment, the oscillatory function may be a sinusoidal function, and, in particular, a cosine function. The process continues at step 422 to determine if the current time $T_i$ is less than the modality treatment session time $T_C$.

If at step 436 it is determined that the control parameter representing the timed transition is not enabled, then the process continues at step 458. At step 458, if the current time is in a low phase (i.e., alternating time variable $T_A$ is not greater than the sum of the high and low tension times ($T_H$+$T_L$)), then the alternating time variable $T_A$ is repeatedly adjusted at step 460 for normalization purposes. Upon the alternating time variable $T_A$ being adjusted to satisfy the criteria of step 458, then the process continues at step 460. If at step 460 it is determined that the alternating time variable $T_A$ is less than the high tension time $T_H$, then the modality profile is in a low tension time $T_L$ and the output tension level $A_O$ is set to a constant low tension level $A_L$ is at step 462. The process thereafter continues at step 422. If, however, the alternating time variable $T_A$ is greater than or equal to the high time variable $T_H$, then the process continues at step 450 and continues as described above.

If at step 440 it is determined that the alternating time variable $T_A$ is no longer in a transition time $T_T$, then the process continues to determine whether the alternating time variable $T_A$ is in a low tension time $T_L$ at step 464. If not, then at step 464 a determination is made as to whether the alternating time variable $T_A$ is in a transition time $T_T$. If so, then a transition tension level is computed at step 466 for increasing the tension from the low tension level $A_L$ to high tension level $A_H$. Otherwise, a determination is made whether the alternating time variable $T_A$ is at a low tension time $T_L$ at step 468. If so, then the output tension level $A_O$ is set to a constant low tension level $A_L$ at step 470. Otherwise, it is assumed the alternating time variable $T_A$ is in a transition time on the down slope and the counter OscCount is reset to zero at step 472 and transition tension level computed at step 474. After each of these computations for the output tension level $A_O$, the process continues at step 422. If the current time $T_i$ is at the modality treatment time $T_C$, the process ends at step 476.

Figure 5:
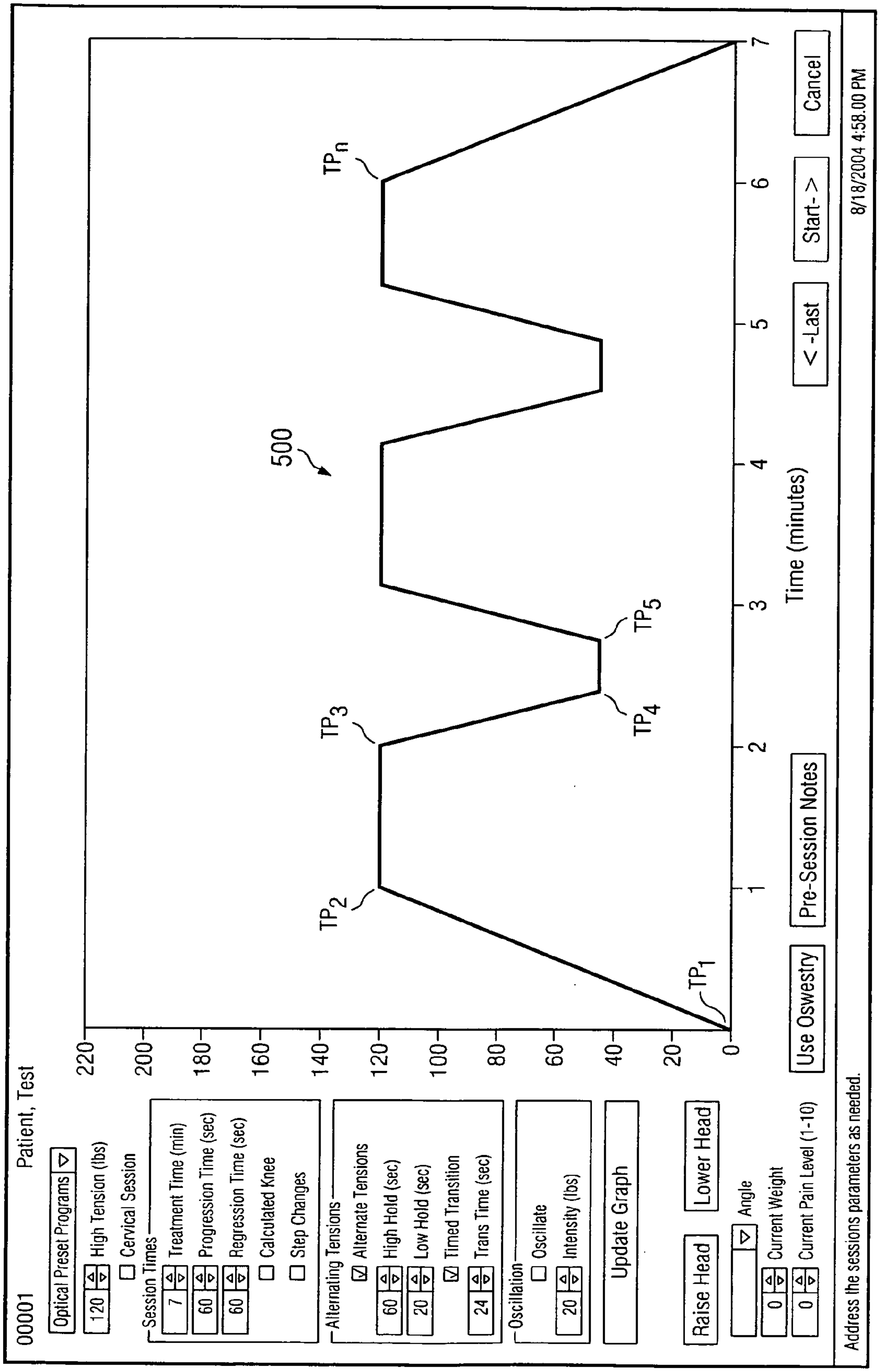
FIG. 5 is a graph of an exemplary conventional modality profile.

FIG. 5 is a graph of an exemplary conventional signal 500 representative of a modality profile for tension levels to be communicated to an electromagnetic actuator to perform a modality treatment on a patient. The conventional signal 500 is composed of a progressive phase extending between transition points $TP_1$ and $TP_2$, modality phase extending between transition points $TP_2$ and $TP_n$, and regression phase extending beyond transition point $TP_n$. As shown, the transition points during the modality phase represent discontinuity or substantially instantaneous slope transition points between the high tension level $A_H$ and transition tension level (e.g., $TP_3$) and transition tension level and low tension level $A_L$ (e.g., $TP_4$). At each of the transition points, because modem modality systems use equipment with accurate and responsive reactions to a signal representative to a modality profile, a near instantaneous motor response may occur, thereby resulting in a burst of acceleration or other sharp transition. This sharp transition may be uncomfortable or possibly problematic for treatment to patients with acute pain or sensitivity problems with a modality machine utilizing conventional modality profiles.

Figure 6:
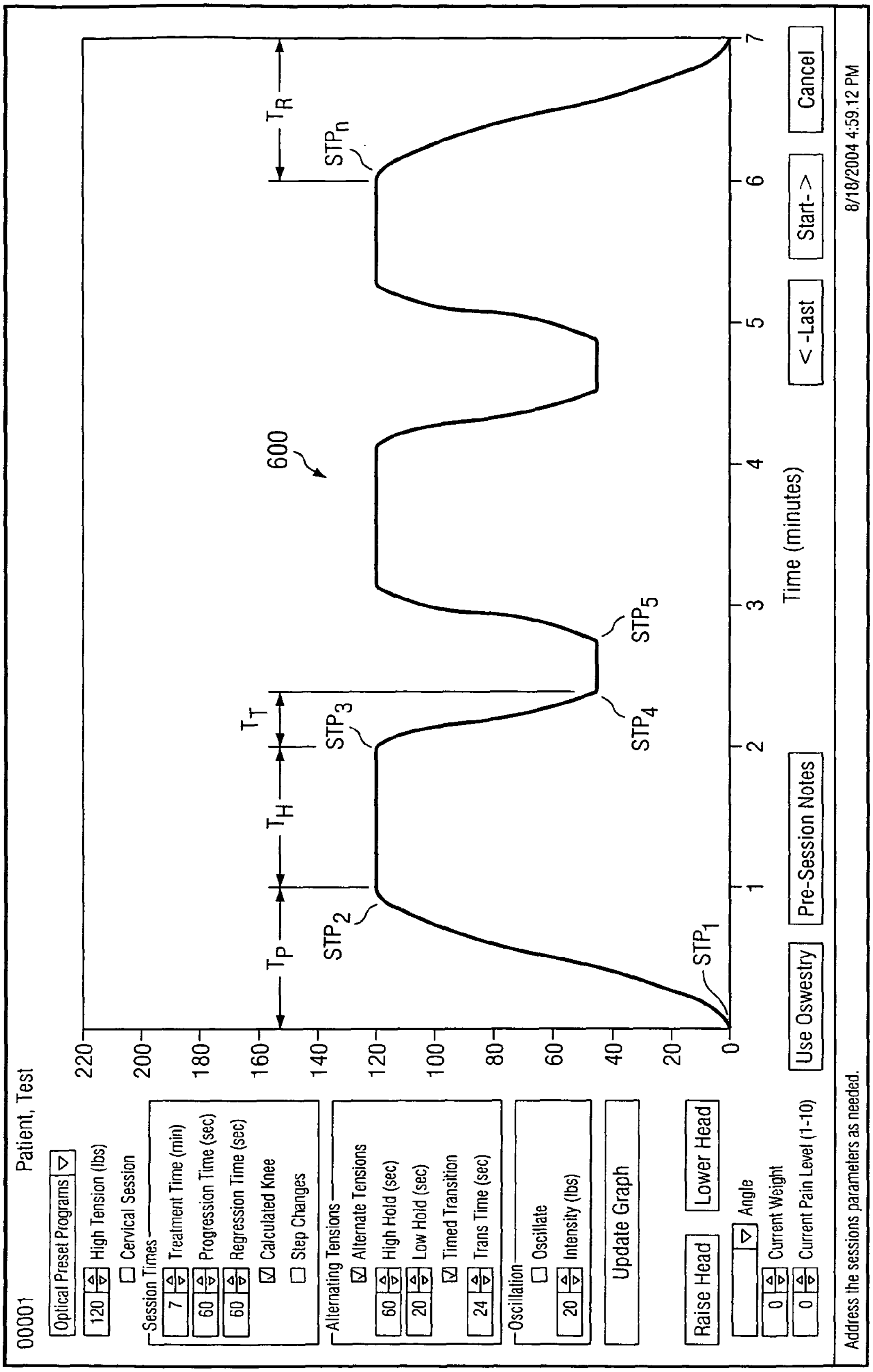
FIG. 6 is a graph of an exemplary modality profile having smooth transition points.

FIG. 6 is a graph of an exemplary signal 600 representing a modality profile having smooth transition points $STP_1$-$STP_n$ (collectively STP). The smooth transition points STP are substantially absent of a discontinuity or substantially instantaneous slope transition during the transition time $T_T$. The smooth transition points STPs may be generated by utilizing a smoothing function, which may include a linear or non-linear function, and produce a modality profile having a gradual acceleration. The smooth transition points STPs, in general, form a curve that is non-linear in at least one portion of the transition between first and second tension levels. By substantially eliminating discontinuities or instantaneous slope transactions on the modality profile, treatment of patients may be improved, especially to those patients who have acute back pain or heightened sensitivity to even slight acceleration bursts resulting from abrupt slope transitions in the modality profile. It should be understood that a sharp, abrupt, or instantaneous slope transition results from two linear functions substantially intersecting at a point.

The smooth transition points STP may be produced via software or hardware. In one embodiment, software operating in a decompression head may compute data points for the signal at each tension level transition, including during the progressive phase $P_P$ and regressive phase $P_R$. For example, smooth transition point $STP_5$ has a non-instantaneous slope change from the low tension level $A_L$ to a high tension level $A_H$ via transition tension levels. In one embodiment, the data points may be computed utilizing a sinusoidal mathematical function. Alternatively, other smoothing functions may be utilized, such as integration. Although not shown, it should be understood that the oscillatory functionality at the high tension level $A_H$ may additionally be included in other portions of the signal 600 according to the principles of the present invention.

Referring still to FIG. 6, the graph is shown as part of a graphical user interface that enables an operator of the modality machine to set and/or adjust (i) control parameters, (ii) signal timing for the modality treatment, and (iii) levels of the modality treatment. For example, the operator may select whether or not to apply an oscillation at a high tension level $A_H$ and the intensity of the oscillation $A_I$. In addition, the operator may select whether to utilize smooth transitioning or "calculated knee" between high and low tension levels during the modality treatment. The selections and level adjustments may be provided to the operator utilizing graphical user interface elements and techniques as understood in the art.

The result of using smooth transitions between phases is more acceptance by the human body for receiving the modality treatment. In general, the human body tends to accept frequency and repetitious pulses in a non-linear, differential manner. The smooth transitions, which may generally be performed in a non-linear manner, provides for more precise control by the modality machine and provides for more consistent treatment results and pain management than conventional linear pull systems.

Figure 7A:
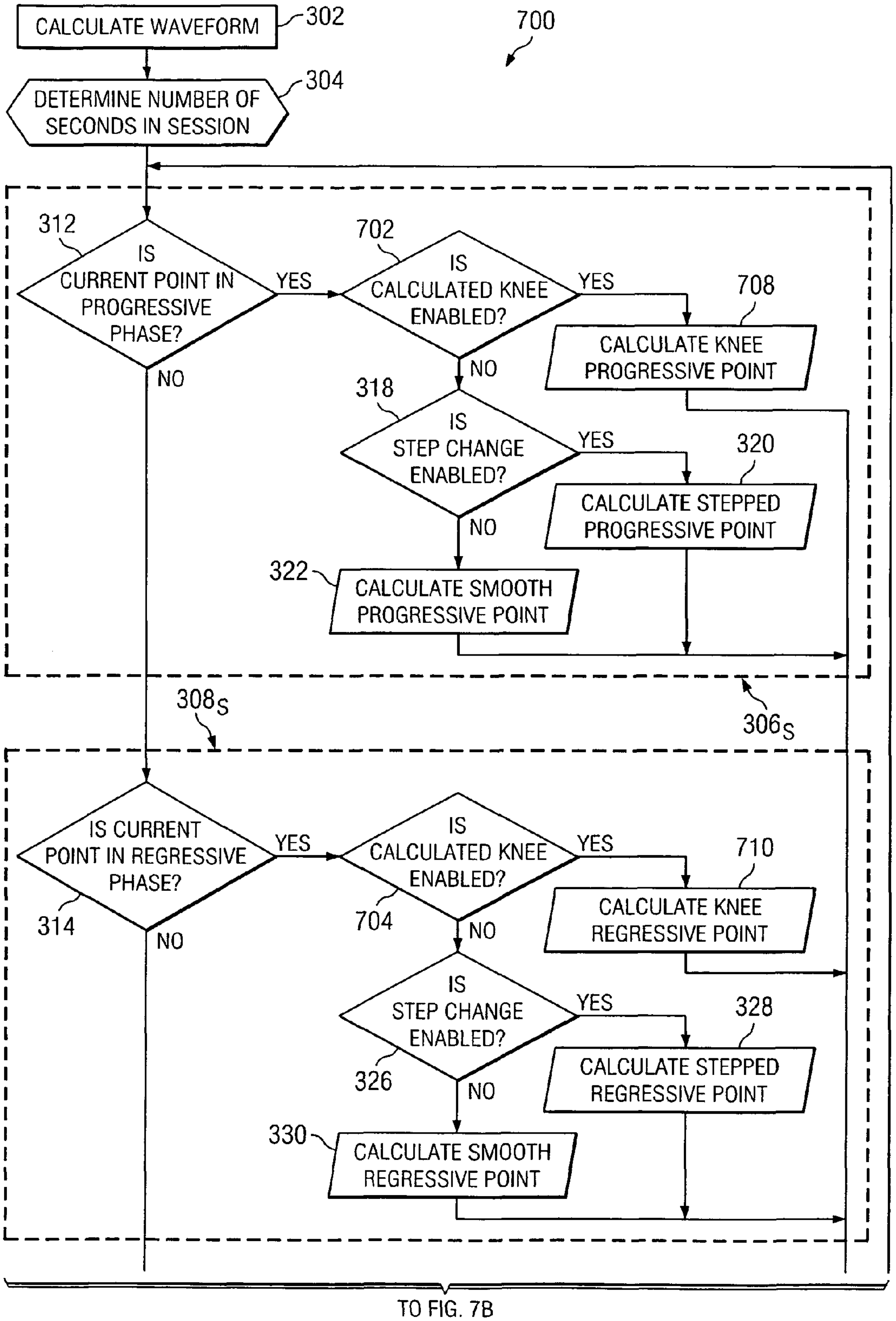
FIGS. 7A-7B (collectively FIG. 7) are flow diagrams of an exemplary algorithm that includes many steps of FIG. 3 with additional steps for determining if a calculated "knee" or smooth transition is enabled for providing a modality treatment.
Figure 7B:
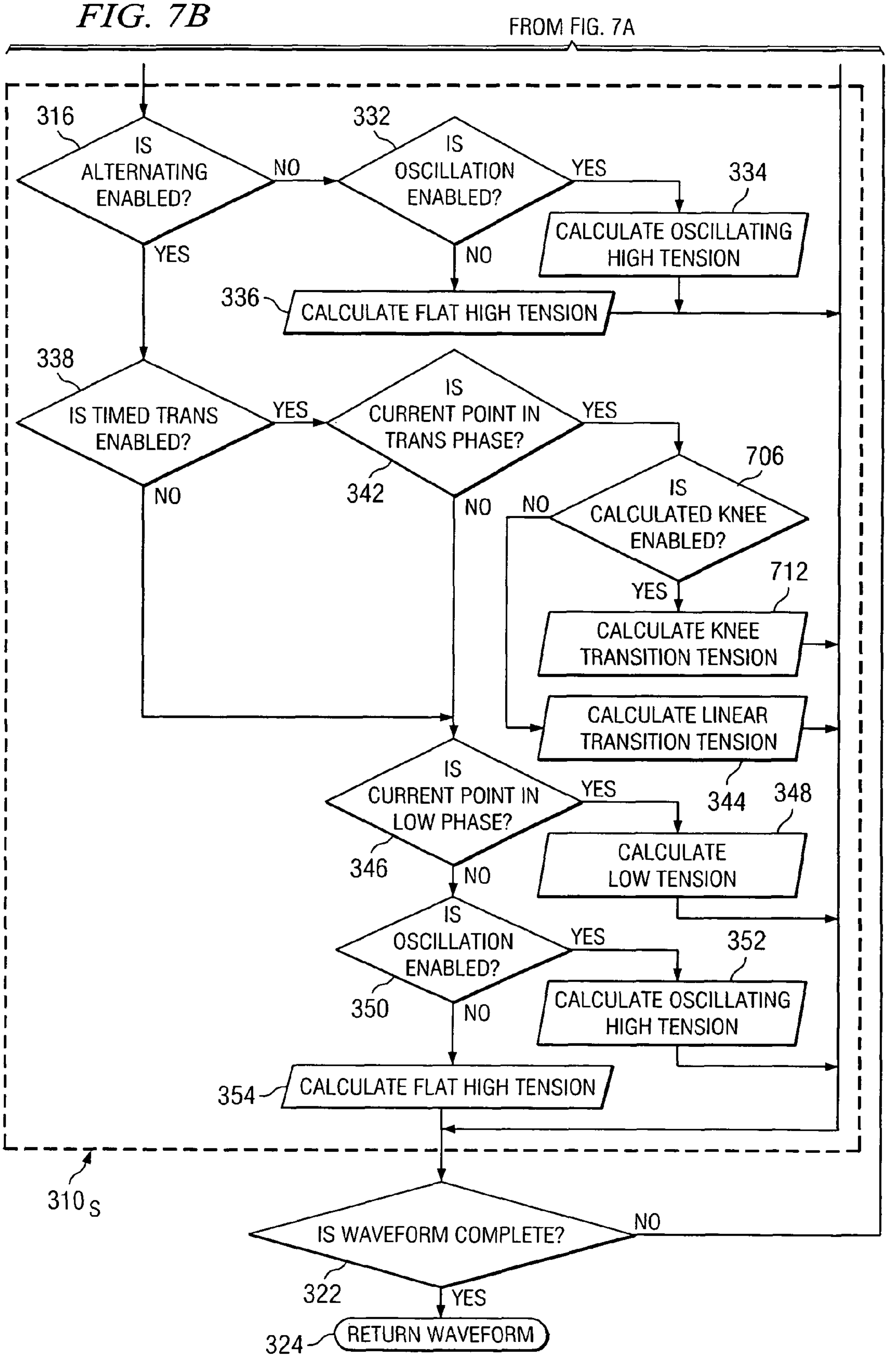

FIG. 7 illustrates a flow diagram of an exemplary algorithm 700 that includes many steps of FIG. 3 with additional steps for determining if a "calculated knee" or smooth transition is enabled. The algorithm sections $\mathbf{306}_S$, $\mathbf{308}_S$, and $\mathbf{310}_S$ provide for calculating a signal during the progressive, regressive and modality phases $P_P$, $P_R$, and $P_M$, respectively, utilizing a smoothing function. The smooth transition determining steps are included at steps 702, 704, and 706 and inspect whether a control parameter for performing a smooth transition is enabled. If it is determined at any of these steps 702, 704, or 706 that smooth transition is enabled, then smooth transition points to progressive, regressive, and transition points of a modality profile may be calculated at steps 708, 710, and 712, respectively. The smooth transition point calculations may be used in combination with either a flat or oscillating high tension during high time $T_H$ (see, FIG. 2).

Figure 8A:
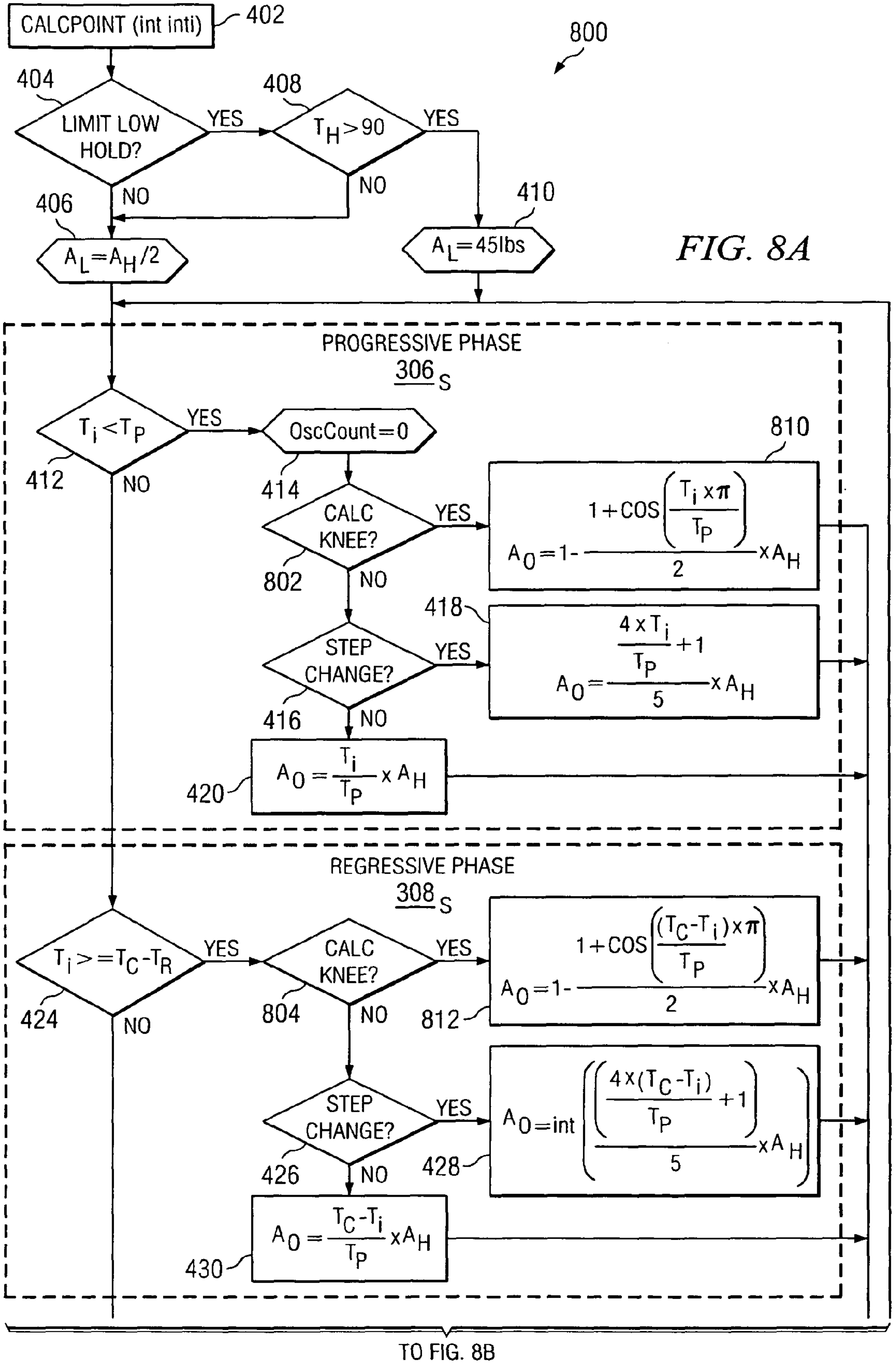
FIGS. 8A-8C (collectively FIG. 8) are more detailed flow diagrams that describe an exemplary algorithm including exemplary mathematical formulae for generating a waveform including smooth transitions between different phases as shown in FIG. 6 to substantially eliminate discontinuities and to generate a modality profile including oscillations on the high tension level as shown in FIG. 2 for providing a modality treatment.
Figure 8B:
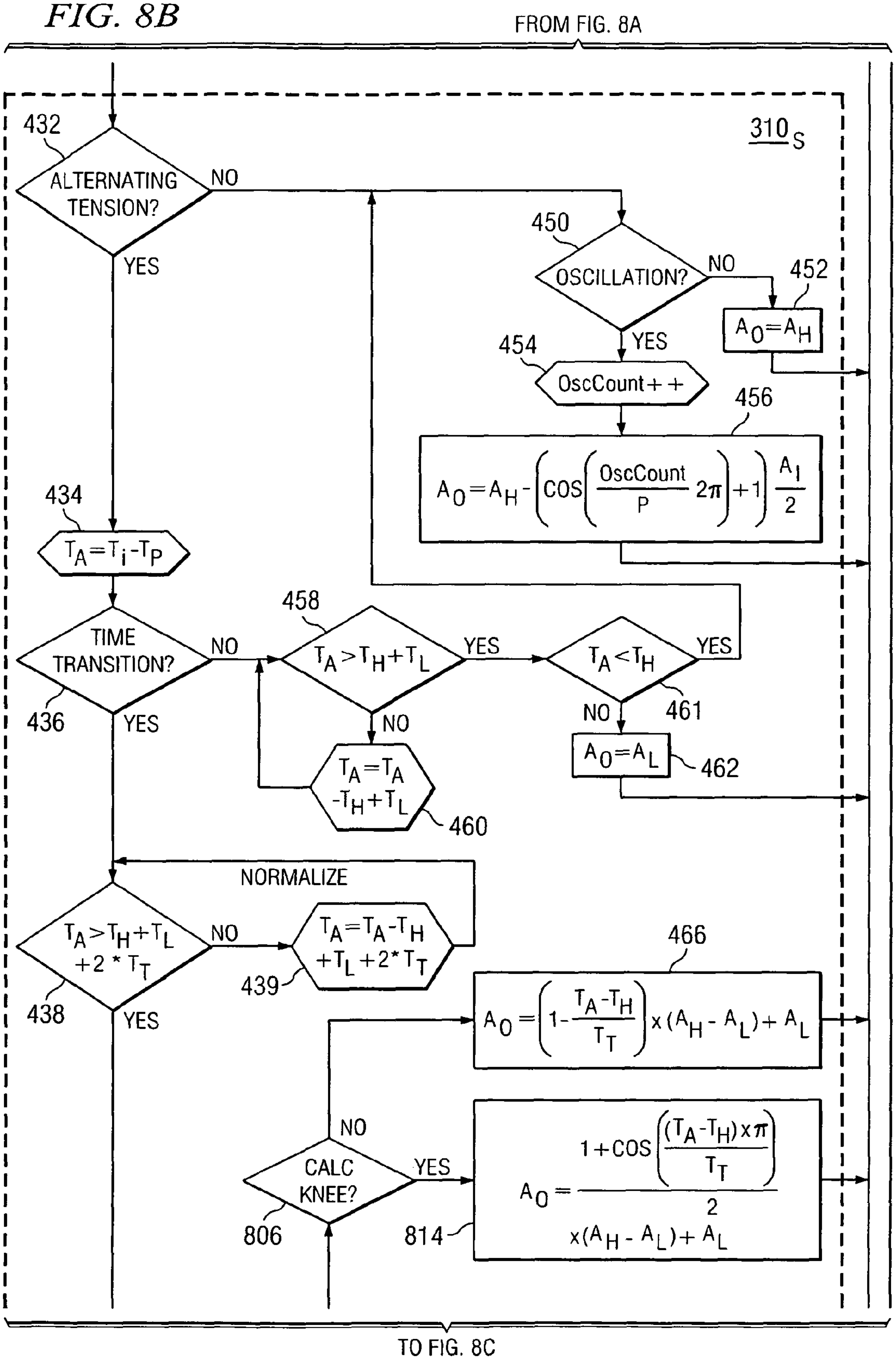
Figure 8C:
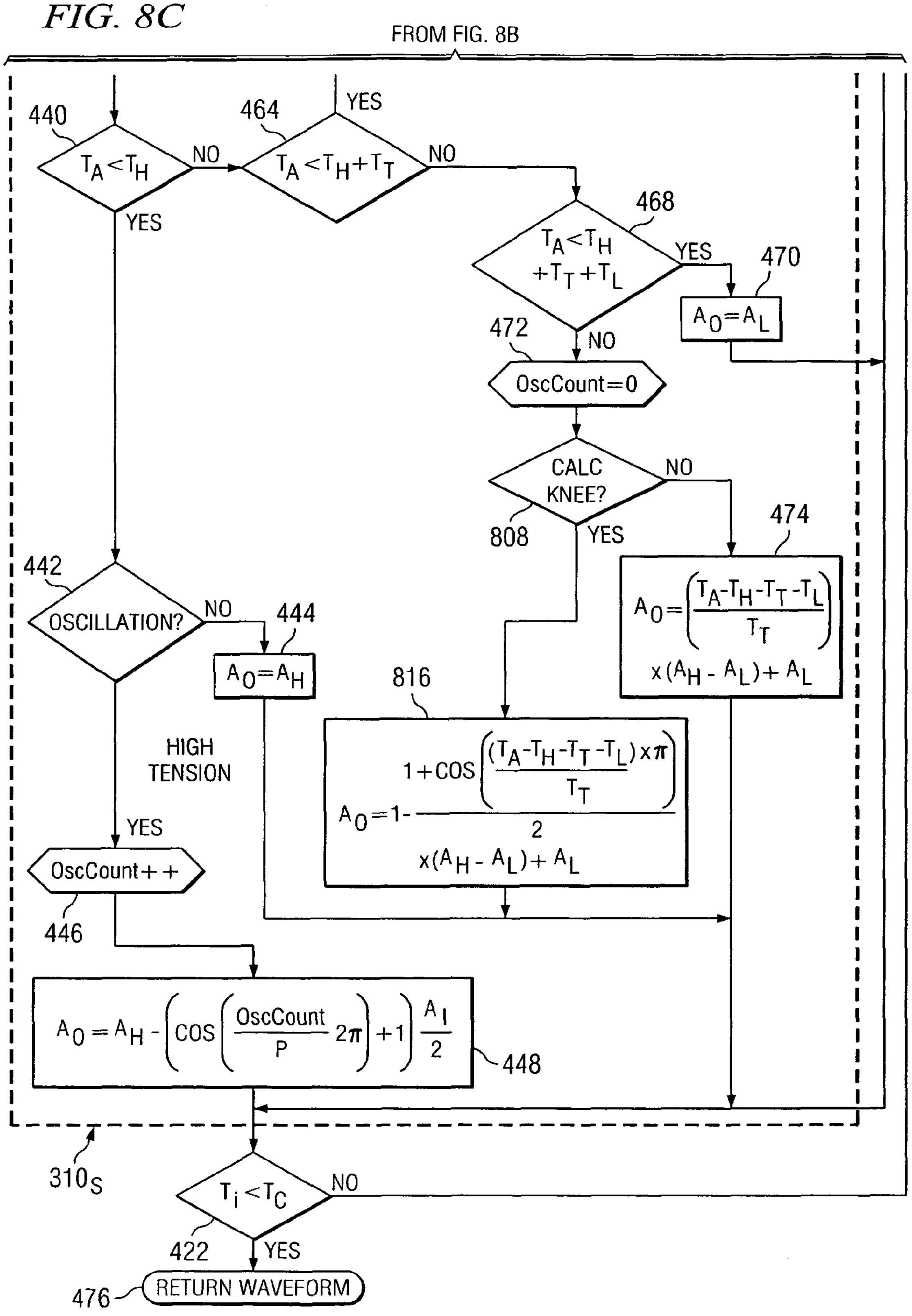

FIG. 8 is a more detailed flow diagram that describes an exemplary algorithm 800 including exemplary mathematical formulae for generating a waveform including smooth transition points between different tension levels (see FIG. 6) to substantially eliminate discontinuities and to generate a signal representing a modality profile including oscillations on the high tension level (see FIG. 2) for a modality treatment. The algorithm 800 describes operations and smoothing functions that are utilized to implement the process or algorithm described in FIG. 7. In one embodiment, one calculation is performed per time interval on a real-time basis during a modality treatment on a patient to compute an output tension level $A_O$. A variable for controlling whether a smooth transition should be employed may be set by an operator of the modality machine. If the smooth transition variable is set and determined at any of steps 802, 804, 806, or 808, then the data points for the output tension level $A_O$ may be calculated by a sinusoidal equation shown in step 810, 812, 814 or 816, depending on the particular transition. As shown, a cosine function may be used for calculating the output tension value $A_O$. However, it should be understood that other smoothing functions that are linear or non-linear may be employed and that any technique for smoothing the transition between different tension levels during a modality treatment may be utilized in accordance with the principles of the present invention.

The innovative concepts described in the present application can be modified and varied over a wide rage of applications. Accordingly, the scope of patented subject matter should not be limited to any of the specific exemplary teachings discussed, but is instead defined by the following claims.

We claim:

1. A modality system for performing modality treatments on patients, said system comprising: a table for supporting a patient; an electromechanical actuator fixedly positioned relative to said table; a patient engaging member configured to engage the patient; a coupling member configured to have tension applied thereto by said actuator and engage said patient engaging member; and a controller operable to communicate a signal to said actuator to cause said actuator to apply tension to said coupling member for applying tension to the patient via said patient engaging member for performing a modality treatment on the patient, said controller computing the signal having a first tension level, a second tension level, and transition tension levels between the first and second tension levels, the higher of the first and second tension levels including an oscillation.

2. The system according to claim 1, wherein said controller calculates the oscillation by mathematically subtracting an oscillatory function from a predetermined tension level.

3. The system according to claim 1, wherein the oscillation is computed from a sinusoidal function.

4. The system according to claim 3, wherein the sinusoidal function is a cosine function.

5. The system according to claim 1, wherein the signal alternately repeats between the first and second tension levels during the modality treatment, said controller computing values for the transition tension levels based on a smoothing function.

6. The system according to claim 5, wherein the smoothing function includes a cosine function.

7. The system according to claim 5, wherein the smoothing function is non-linear.

8. The system according to claim 1, wherein the modality treatment includes intradiscal disc decompression.

9. The system according to claim 1, wherein said electromechanical actuator is a motor.

10. The system according to claim 1, wherein said coupling member is a cable.

11. The system according to claim 1, wherein said patient engaging member is a harness.

* * * * *